United States Patent
Manoharan

(10) Patent No.: US 8,524,178 B2
(45) Date of Patent: Sep. 3, 2013

(54) DOPED ALUMINUM OXIDES

(75) Inventor: S. Sundar Manoharan, Kanpur (IN)

(73) Assignee: Indian Institute of Technology Kanpur, Kanpur (IN)

( * ) Notice: Subject to any disclaimer, the term of this patent is extended or adjusted under 35 U.S.C. 154(b) by 5 days.

(21) Appl. No.: 13/321,146

(22) PCT Filed: Apr. 15, 2011

(86) PCT No.: PCT/IB2011/051642
§ 371 (c)(1),
(2), (4) Date: Nov. 17, 2011

(87) PCT Pub. No.: WO2012/110858
PCT Pub. Date: Aug. 23, 2012

(65) Prior Publication Data
US 2013/0009098 A1   Jan. 10, 2013

(30) Foreign Application Priority Data
Feb. 14, 2011   (IN) .............................. 385/DEL/2011

(51) Int. Cl.
*C01F 1/00*   (2006.01)
*C01F 3/00*   (2006.01)
*C01F 7/00*   (2006.01)
*C01F 15/00*   (2006.01)
*C09K 11/02*   (2006.01)
*C09K 11/08*   (2006.01)
*C09K 11/77*   (2006.01)
*C04B 35/00*   (2006.01)

(52) U.S. Cl.
USPC .................... 423/122; 423/600; 252/301.4 R; 501/127; 501/153

(58) Field of Classification Search
USPC ................. 501/94, 96.1, 96.2, 108, 109, 123, 501/125, 126, 127, 152, 153; 252/301.4 R, 252/301.6 R, 301.4 S, 301.4 P, 301.4 F, 301.4 252/H, 301.6 S, 301.6 P, 301.6 F; 423/122, 423/600
See application file for complete search history.

(56) References Cited

U.S. PATENT DOCUMENTS

| | | | |
|---|---|---|---|
| 3,725,094 A | 4/1973 | Levy | |
| 4,084,983 A * | 4/1978 | Bernhard et al. | 106/402 |
| 5,637,547 A * | 6/1997 | Chopin et al. | 502/415 |
| 5,679,466 A * | 10/1997 | Noguchi et al. | 428/551 |

FOREIGN PATENT DOCUMENTS

JP   55-162477   12/1980

OTHER PUBLICATIONS

Mei. Synthesis, characterization and thermal properties of metaloquinolate-containing polymers. European Polymer Journal 43 (2007) 2380-2386.*

Colle, M., et al., "The Structure of the Blue Luminescent δ-Phase of Tris(8-hydroxyquinoline)aluminium(III) ($Alq_3$)," Chemical Communications, 2002, pp. 2908-2909.

Crespi, M.S. et al., "Thermal behavior of the Ti(IV), Zr(IV) and Pb(II) Complexes with 5-nitro-8-hydroxyquinoline," Journal of Thermal Analysis and Calorimetry, 2003, vol. 72, pp. 507-514.

Dubey, B.L. et al., "Thermal behaviour of 8-hydroxyquinoline complexes with nickel(II)/copper(II)/zinc(II) hydroxides," Journal of Thermal Analysis, 1997, vol. 48, pp. 885-891.

Guerreiro, C.T.R. et. al., "Synthesis and Thermal Study of 8-Hydroxyquinoline Derivatives of the Alkaline Earth Metals—I. Strontium Complexes," Journal of Thermal Analysis and Calorimetry, 1999, vol. 56, pp. 519-524.

Kampf, L., "Volumetric Determination of Iron and Aluminum in Cement with 8-Hydroxyquinoline," Industrial and Engineering Chemistry, 1941, vol. 13, No. 2, pp. 72-73.

Katakura, R. et al., "Configuration-specific synthesis of the Facial and Meridional Isomers of Tris(8-hydroxyquinolinate)aluminum (Alq(3))," Inorganic Chemistry, 2006, published on web Jun. 30, 2006, vol. 45, No. 15, pp. 5730-5732.

Kokkonen, P. et al., "Thermal Decomposition of 8-hydroxyquinoline Complexes with Aluminum, Cobalt, Manganese and Nickel," Thermochimica Acta, Apr. 15, 1987, vol. 114, pp. 329-336.

Montes, V. et al., "Effective Manipulation of the Electronic Effects and Its Influence on the Emission of 5-Substituted Tris(8-quinolinolate) Aluminum(III) Complexes," Chemistry—A European Journal, 2006, vol. 12, pp. 4523-4535.

Chen, W. et al., "$Alq_3$ Nanorods: Promising Building Blocks for Optical Devices," Advanced Materials, vol. 20, Issue 14, pp. 2747-2750, Jul. 17, 2008.

Chung-Jun, L., et al., "Organic Light Emitting Diodes Using Doped $Alq_3$ as the Hole-Transporter Layer," Chin Phys Lett, vol. 25, No. 5, pp. 1832-1835, (2008).

Rajeswaran, M. et al., "Single-crystal structure determination of a new polymorph (e-$Alq_3$) of the electroluminescence OLED (organic light-emitting diode) material, tris(8-hdroxyquinoline) aluminium ($Alq_3$)," Journal of Chem Crystallography, vol. 35, No. 1, pp. 71-76, Jan. 2005.

* cited by examiner

*Primary Examiner* — Carol M Koslow
*Assistant Examiner* — Matthew E Hoban
(74) *Attorney, Agent, or Firm* — Foley & Lardner LLP

(57) ABSTRACT

A process of preparing a doped aluminum oxide, includes providing a solution comprising 8-hydroxyquinoline; an aluminum precursor; a dopant precursor, and a reaction solvent; isolating a precipitate from the solution; and calcining the precipitate to form the doped aluminum oxide. Compositions may be prepared which include tris(8-hydroxyquinolinato) aluminum and (8-hydroxyquinolinato)$_z$M, wherein M is a metal ion and the value of z is equivalent to the oxidation state of the metal ion.

18 Claims, 1 Drawing Sheet

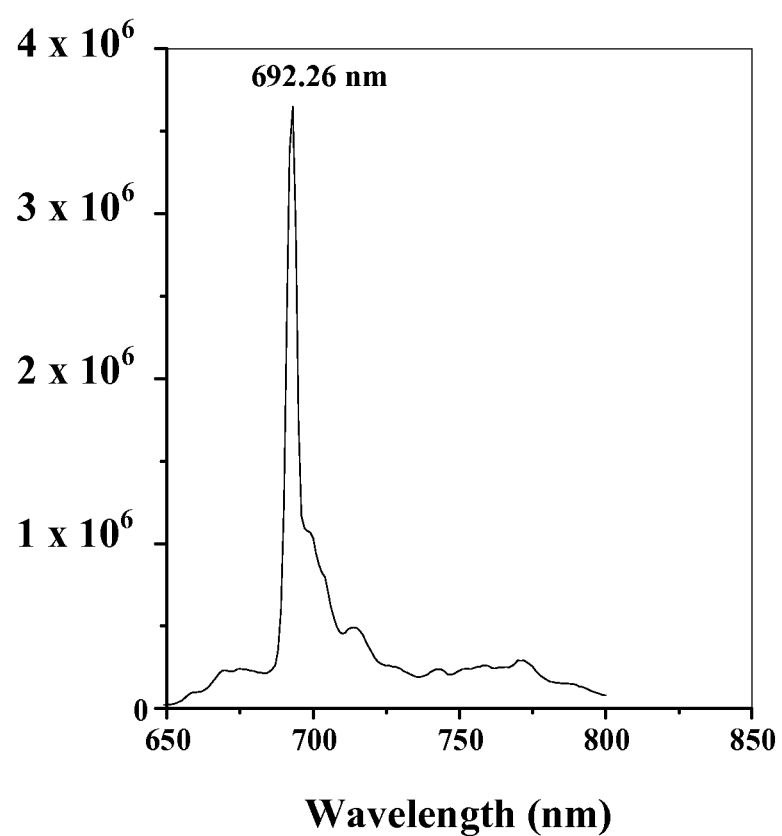

DOPED ALUMINUM OXIDES

CROSS-REFERENCE TO RELATED APPLICATIONS

This application is a national stage application of International Application Serial No. PCT/IB2011/051642, filed on Apr. 15, 2011, which in turn claims the benefit of priority of Indian Application No. 385/DEL/2011, filed on Feb. 14, 2011, the entire disclosures of which are each hereby incorporated by reference for all purposes in their entireties as if fully set forth herein.

FIELD

The technology generally relates to inorganic oxides. In particular, the technology relates to aluminum oxides.

BACKGROUND

Doped aluminum-based inorganic oxides such as garnets (Y3Al5O12), Nd:YAG, perovskites, and ruby find widespread use as phosphors, pigments, catalysts, and lasing materials. Despite a broad interest, general synthetic methods to prepare such doped oxides are lacking, due to at least two reasons. First, it is a significant challenge to ensure homogeneous and atomic-scale dispersion of the dopant atom(s) within the aluminum oxide matrix. Second, it is difficult to prepare a given doped aluminum oxide in a variety of physical formats such as powders, films, or wires. Moreover, most synthetic methods require stringent processing conditions (e.g. physical and chemical deposition methods), or exceedingly high temperatures (e.g. ruby crystal growth or calcination of YAG materials produced via sol-gel techniques).

SUMMARY

In one aspect, a process of preparing a doped aluminum oxide includes providing a solution including 8-hydroxyquinoline, an aluminum precursor, a dopant precursor, and a reaction solvent. The process further includes isolating a precipitate from the solution and further calcining the precipitate to form the doped aluminum oxide.

In another aspect, a composition is provided which includes tris(8-hydroxyquinolinato) aluminum and (8-hydroxyquinolinato)$_z$M, where M is a metal ion and the value of z is equivalent to the oxidation state of the metal ion. In another aspect, a polymer composite is provided including a polymer, tris(8-hydroxyquinolinato)aluminum and (8-hydroxyquinolinato)$_z$M, where M and z are defined above.

BRIEF DESCRIPTION OF THE DRAWINGS

FIG. 1 is an emission spectrum of Cr:Al$_2$O$_3$ (i.e., ruby powder) prepared according to Example 2A.

DETAILED DESCRIPTION

The bidentate ligand 8-hydroxyquinoline reacts with a variety of metal ions to give (8-hydroxyquinolinato) metal complexes ((a) Guerreiro, C. T. R. et al. *Journal of Thermal Analysis and Calorimetry* (1999), 56, 519-524; (b) Kokkonen, P. et al. *Thermochimica Acta* (1987), 114, 329-336; (c) Crespi, M. S. et al. *Journal of Thermal Analysis and Calorimetry* (2003), 72, 507-517; (d) Dubey, B. L. et al. *Journal of Thermal Analysis* (1997), 48, 885-891). The number of quinolinato ligands (anionic two-electron donor ligands) bound to the metal ion is determined by the oxidation state of the metal ion. For example, Sr(II) or Zn(II) precursors (e.g., SrCl$_2$ or Zn(OEt)$_2$), upon reaction with 8-hydroxyquinoline, will give bis(8-hydroxyquinolinato)strontium or bis(8-hydroxyquinolinato)zinc, respectively. Likewise, metal precursors in the +3 oxidation state, will yield tris(8-hydroxyquinolinato) metal complexes.

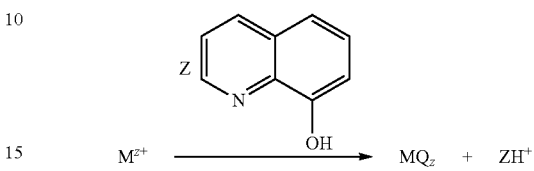

In one aspect, a process is provided including reacting an aluminum precursor and a dopant precursor with 8-hydroxyquinoline in a reaction solvent to yield a precipitate. The precipitate thus formed includes mixed quinolate species, i.e., tris(8-hydroxyquinolinato)aluminum and the 8-hydroxyquinolinato complex of the dopant, is then isolated from the solution. In this case, the 8-hydroxyquinolinato complex of the dopant is homogeneously dispersed within the tris(8-hydroxyquinolinato)aluminum on an atomic scale. Thus, the precipitate is a solid solution. As used herein, a "solid solution" refers to a crystalline material containing a second constituent which fits into and is distributed in the lattice of the host crystalline material. The precipitate may be used as a precursor to prepare doped aluminum oxides. In particular, by calcining the precipitate, a doped aluminum oxide is obtained, in which atoms or ions from the 8-hydroxyquinolinato complex of the dopant are likewise homogeneously dispersed within the aluminum oxide. Where the dopant precursor includes a metal, the process outlined above provides a solid solution of tris(8-hydroxyquinolinato)aluminum and the 8-hydroxyquinolinato complex of the metal in the form of a precipitate. Likewise, this precipitate may be calcined to provide aluminum oxide doped with metal atoms or ions, with such metal atoms or ions being dispersed within the aluminum oxide on an atomic scale.

Thus, in another aspect, a process is provided that includes preparing a solution of 8-hydroxyquinoline, an aluminum precursor, a dopant precursor, and a reaction solvent. The process also includes isolating a precipitate from the solution and calcining the precipitate to form the doped aluminum oxide.

The dopant precursor may include a metal salt or a metal alkoxide. If a metal salt is used as the dopant precursor, the only requirement of the metal salt is that the anion of the metal salt be capable of being displaced by a ligand (such as 8-hydroxyquinoline or its anionic equivalent). Thus, the metal salt may include, but is not limited to: a metal fluoride, a metal chloride, a metal bromide, a metal iodide, a metal nitrate, a metal phosphate, a metal sulfate, a metal tetrafluoroborate, a metal hexafluorophosphate, a metal formate, a metal acetate, a metal picrate, a metal triflate, a metal mesylate, a metal sulfonate, a metal carbonate, and a metal hydrogencarbonate. In some embodiments, the metal salt is a metal nitrate, a metal chloride, or a metal acetate. If a metal alkoxide is used, the only requirement of the metal alkoxide is that the alkoxide anion of the metal alkoxide be capable of being displaced by a ligand (such as 8-hydroxyquinoline or its anionic equivalent). The term "alkoxide" as used herein refers to an —OR group, where R is a C$_1$-C$_{10}$ alkyl, C$_1$-C$_{10}$ alkenyl, C$_1$-C$_{10}$ alkynyl, C$_3$-C$_6$ aryl, or a substituted analog thereof. In one embodiment, a metal ethoxide is used as a dopant precursor. Other suitable metal alkoxides include metal methoxides, metal n-propoxides, metal isopropoxides, metal tert-butoxides, metal phenoxides, etc.

Where the dopant precursor is a metal salt or a metal alkoxide, the metal may be, but is not limited to, chromium, manganese, iron, cobalt, nickel, lanthanum, cerium, praseodymium, neodymium, promethium, samarium, europium, gadolinium, terbium, dysprosium, holmium, erbium, thulium, ytterbium, lutetium, yttrium, calcium, magnesium, barium, or strontium. The metal of the metal salt or metal alkoxide may have an oxidation state of +1, +2, +3, +4, +5, or +6. In some embodiments, the metal is one of chromium, cobalt, nickel, lanthanum, yttrium, or strontium and is in the form of a nitrate salt, a chloride salt, an acetate salt, or an ethoxide. In some embodiments, the dopant precursor is chromium(III) chloride, cobalt(II) chloride, nickel(II) chloride, lanthanum(III) chloride, yttrium(III) chloride, strontium (II) chloride, chromium(III) nitrate, cobalt(II) nitrate, nickel (II) nitrate, lanthanum(III) nitrate, yttrium(III) nitrate, strontium(II) nitrate, chromium(III) acetate, cobalt(II) acetate, nickel(II) acetate, lanthanum(III) acetate, yttrium (III) acetate, strontium(II) acetate, chromium(III) ethoxide, cobalt(II) ethoxide, nickel(II) ethoxide, lanthanum(III) ethoxide, yttrium(III) ethoxide, or strontium(II) ethoxide.

In other embodiments, two or more dopant precursors are used together and in any proportion. For example, a mixture of yttrium(III) nitrate, lanthanum(III) triflate, and strontium (II) ethoxide in a 1:2:3 molar ratio may be employed as the dopant precursor. Such a mixture would allow for the preparation of doped aluminum oxide doped with three different ions: yttrium(III), lanthanum(III), and strontium(II) in unequal proportion. As a second example, a mixture of chromium(II) chloride and chromium(III) nitrate 1:2 ratio may be employed as the dopant precursor. Such a mixture would allow for the preparation of a doped aluminum oxide doped with ions of the same element but with different oxidation states: chromium(II) and chromium(III).

The aluminum precursor used in the reaction may include, but is not limited to an aluminum salt, an aluminum alkoxide, or a mixture of any two or more thereof Aluminum salts include, but are not limited to, aluminum fluoride, aluminum chloride, aluminum bromide, aluminum iodide, aluminum acetate, aluminum sulfate, aluminum perchlorate, aluminum phosphate, and the like. Aluminum alkoxides have the general formula Al(OR)$_3$, where R is a $C_1$-$C_{10}$ alkyl, $C_1$-$C_{10}$ alkenyl, $C_1$-$C_{10}$ alkynyl, $C_3$-$C_6$ aryl, or a substituted analog thereof In some embodiments, R is methyl, ethyl, n-propyl, or isopropyl. The aluminum precursor may, alternatively be, or include one or more triorganoaluminums. Such triorganoaluminums have the general formula AlR$_3$, where R is a $C_1$-$C_{10}$ alkyl, $C_1$-$C_{10}$ alkenyl, $C_1$-$C_{10}$ alkynyl, $C_3$-$C_6$ aryl, or a substituted analog thereof. In some embodiments, R is methyl.

The molar ratio of the aluminum precursor to the dopant precursor may vary, depending upon the desired incorporation of the dopant in the aluminum oxide (or in the precipitate, i.e., the solid solution which may be further calcined to prepare the doped aluminum oxide). In one embodiment, the molar ratio of the dopant precursor to the aluminum precursor is from about 2.0:3.0 to about 3.0:5.0, or from about 0.95:1.0 to about 0.66:1.0. In another embodiment, the molar ratio of the dopant precursor to the aluminum precursor is from about 0.05:1.0 to about 0.334:0.666. In yet another embodiment, the molar ratio of the dopant precursor to the aluminum precursor is from about 0.05:1.0 to about 0.33:1.0.

A variety of reaction solvents may be employed in the process, including, but not limited to, water, alcohols, ethers, glycol ethers, ketones, amides, nitriles, hydrocarbons, halogenated hydrocarbons, or mixtures of any two or more thereof. In some embodiments, the reaction solvent includes, but is not limited to, methanol, ethanol, n-propanol, isopropanol, n-butanol, tert-butanol, diethyl ether, diisopropyl ether, dibutyl ether, tetrahydrofuran, 2-methyltetrahydrofuran, monoglyme, diglyme, acetone, 2-butanone, N,N-dimethylformamide, N,N-dimethylacetamide, N-methylpyrrolidinone, acetonitrile, hexane, toluene, xylenes, dichloromethane or chloroform. In one embodiment, the reaction solvent includes methanol, ethanol, n-propanol, isopropanol, diethyl ether, or a mixture of any two or more thereof. In another embodiment, the reaction solvent includes ethanol.

According to another aspect, a precipitate is formed from the reaction of 8-hydroxyquinoline, an aluminum precursor, and a dopant precursor in a reaction solvent. As previously set forth, such a precipitate is a solid solution of the tris(8-hydroxyquinolinato)aluminum and a 8-hydroxyquinolato complex of the dopant. Thus, where the dopant precursor includes a metal ion, a composition including tris(8-hydroxyquinolinato)aluminum and (8-hydroxyquinolinato)$_z$M is provided, wherein M is the metal ion and the value of z is equivalent to the oxidation state of the metal ion. In some embodiments, M is an ion of chromium, iron, cobalt, nickel, lanthanum, cerium, praseodymium, neodymium, promethium, samarium, europium, gadolinium, terbium, dysprosium, holmium, erbium, thulium, ytterbium, lutetium, yttrium, or strontium. In some embodiments, M is an ion of chromium, cobalt, lanthanum, yttrium, or strontium. In still other embodiments, a molar ratio of tris(8-hydroxyquinolinato) aluminum to (8-hydroxyquinolinato)$_z$M is about 0.95:0.05 to about 0.05:0.95 or is about 0.40:0.60 to about 0.60:0.40. In one particular embodiment, the molar ratio of tris(8-hydroxyquinolinato)aluminum to (8-hydroxyquinolinato)$_z$M is about 0.95:0.05, M is chromium, and the value of z is three. In another embodiment, the molar ratio of tris(8-hydroxyquinolinato)aluminum to (8-hydroxyquinolinato)$_z$M is about 0.5: 0.5; M is lanthanum, and the value of z is three.

As will be appreciated, the process may include heating the mixture of reactants and solvents at a temperature and for a time period sufficient to produce the precipitate, prior to the isolation step. In one embodiment, the solution is heated at an elevated temperature (i.e., a temperature above room temperature), up to and including the refluxing temperature of the reaction solvent. In another embodiment, the solution is heated for a time period of about 10 minutes to about 10 hours, about 30 minutes to about 10 hours, about 30 minutes to about 6 hours, about 10 minutes to about 8 hours, about 30 minutes to about 8 hours, about 1 hour to about 8 hours, about 3 hours to about 8 hours, about 4 hours to about 6 hours, or is about 5 hours. Furthermore, other steps known in the art may be employed to aid in the formation of the precipitate (e.g. cooling, evaporation, concentration, addition of seed crystals or other precipitants, and the like).

The precipitate thus formed may be isolated or collected from the solution in any number of ways commonly known in the art. For example, the precipitate may be isolated by decantation, centrifugation, filtration, or other similar technique. The isolated precipitate may optionally be washed with an appropriate wash solvent, such as an alcohol or an ether. In one embodiment, the wash solvent is the same as the reaction solvent. The isolated precipitate may be further dried at or below atmospheric pressure to remove residual reaction solvent or wash solvent. Such drying may further include heating the precipitate to a temperature of about 25° C. to about 250° C., to about 50° C. to about 150° C., or to about 25° C. to about 100° C.

Those of skill in the art will appreciate that the above process for obtaining precipitates may be modified in a number of ways. For example, while the above process employs both an aluminum precursor and a dopant precursor in the presence of 8-hydroxyquinoline in a reaction solvent, it is also possible to use tris(8-hydroxyquinolinato)aluminum directly along with a dopant precursor in the presence of 8-hydroxyquinoline in a reaction solvent. In such a case, 8-hydroxyquinoline need only be added in sufficient quantity to react with the dopant precursor, since aluminum is "pre-complexed" to the quinoline ligand. Following the same reasoning, the dopant may be pre-complexed quinoline ligand and an aluminum precursor used in the presence of 8-hydroxyquinoline in a reaction solvent. In a third alternative, both the tris(8-hydroxyquinolinato)aluminum complex and the 8-hydroxyquinolinato dopant complex may be added to a solvent (such as the reaction solvents described herein), dissolved, and precipitated to give the precipitate.

After isolation, the precipitate may then be calcined to provide a doped aluminum oxide. As used herein, the terms "calcine" or "calcination" refer to heating in the presence of air or oxygen. Other gases, such as argon, may also be present. Calcination is typically carried out in ovens, furnaces, reactors, or kilns of various designs including shaft furnaces, rotary kilns, multiple hearth furnaces, fluidized bed reactors, and the like. In one embodiment, calcination is performed at a temperature from about 400° C. to about 2000° C., from about 500° C. to about 1500° C., from about 400° C. to about 1000° C., from about 300° C. to about 1200° C., from about 400° C. to about 1000° C., from about 400° C. to about 800° C., or from about 500° C. to about 600° C. In some embodiments, the doped aluminum oxides $LaAlO_3$ (perovskite), $Y_3Al_5O_{12}$ (yttrium aluminum garnet, "YAG"), $Cr:Al_2O_3$, $CoAl_2O_4$, or $SrAl_2O_4$ are provided. In further embodiments, calcination of the precipitate gives the doped aluminum oxide in the form of a powder.

Doped aluminum oxides may also be obtained in the form of thin films. In such a process, the precipitate is dissolved in a suitable solvent and cast into a thin film on to a substrate using conventional casting methods. In some embodiments, a thin film is produced by spin-casting. Calcination of the resultant thin film provides a corresponding doped aluminum oxide as a thin film.

In other embodiments, doped aluminum oxides may be prepared in the form of nanofibers. In particular, after isolating a precipitate, the precipitate may be further combined with a polymer to form a polymer composite. The precipitate and polymer may be combined by dissolution of each in a solvent followed by mixing and subsequent solvent evaporation, by adding the precipitate to a liquid or molten polymer, or by other means. Fibers or nanofibers may be prepared from the polymer composite. In one embodiment, fibers or nanofibers of the polymer composite may be prepared through electrospinning techniques. Subsequent calcination of the polymer composite nanofibers provides the doped aluminum oxide in the form of nanofibers. In one embodiment, the polymer may be polyvinylpyrrolidone or polyvinyl alcohol. In another embodiment, the weight ratio of precipitate to polymer is from about 0.05:0.95 to about 0.30:0.70, or from about 0.02:0.98 to about 0.25:0.75. Thus, in one aspect, the present technology provides for a polymer composite which includes a polymer, tris(8-hydroxyquinolinato)aluminum, and (8-hydroxyquinolinato)$_z$M, wherein M is a metal ion and the value of z is equivalent to the oxidation state of the metal ion. In one embodiment of the polymer composite, M is an ion of chromium, cobalt, nickel, lanthanum, cerium, praseodymium, neodymium, promethium, samarium, europium, gadolinium, terbium, dysprosium, holmium, erbium, thulium, ytterbium, lutetium, yttrium, or strontium. In another embodiment of the polymer composite, the polymer is polyvinylpyrrolidone or polyvinyl alcohol.

EXAMPLES

The present technology, thus generally described, will be understood more readily by reference to the following examples, which is provided by way of illustration and is not intended to be limiting of the present technology.

Example 1A

General procedures for preparation $Alq_3$. To a stirring solution of a $Al(NO_3)_3 \cdot xH_2O$ (1.00 g, 2.67 mmol) in ethanol (20 mL) was added 8-hydroxyquinoline (8.00 mmol). An equivalent molar amount of aluminum isopropoxide could also be substituted for $Al(NO_3)_3 \cdot xH_2O$ with equal effectiveness. The reaction mixture or solution was refluxed at about 60° C. for approximately 5 hours. After cooling to room temperature, the resultant $Alq_3$ was collected as a precipitate. The precipitate was washed and dried in vacuo. Analysis of the Alqa precipitate by X-ray diffraction revealed that the phase corresponds to aluminum clathrate with a characteristic 100% peak at around 10 degrees of the two theta value. This major peak is distinctly different from the other phases of $Alq_3$ namely, mer isomer and fac isomer where the 10 degree peak is absent. Hence, this particular XRD reflection serves as a fingerprint for the clathrate structure. Finally, SEM imaging of $Alq_3$ revealed the material to be a highly crystalline material, with spherical crystals generally being unagglomerated and monodisperse in size.

Example 1B

Preparation of solid solutions using an aluminum precursor. The preparation was similar to the procedure described in Example 1A, but a dopant precursor was also added to the solution. To a stirring a solution of $Al(OPr^i)_3$ ($AlCl_3$, $AlBr_3$, $Al(OMe)_3$, $Al(OEt)_3$, $Al(NO_3)_3$, or similar aluminum precursors could also be used) in ethanol was added a dopant precursor followed by 8-hydroxyquinoline. The quantity of dopant precursor was adjusted based upon the desired level of incorporation of the dopant in the solid solution. 8-Hydroxyquinoline was added in sufficient quantity to ensure essentially complete consumption of both the aluminum precursor and the dopant precursor. The order of addition was immaterial. The reaction mixture or solution was refluxed at about 60° C. for approximately 5 hours. After cooling to room temperature, the resultant solid solution was collected as a precipitate. The precipitate was washed and dried in vacuo.

TABLE 1

Solid Solutions Prepared According to Example 1B.

| Entry | Dopant Precursor | General Solid Solution Formula | Specific Solid Solution Prepared | Atom Percent of Dopant |
|---|---|---|---|---|
| 1 | $La(NO_3)_3$ | $La_xAl_{1-x}q_3$ | $La_{0.5}Al_{0.5}q_3$ | 50% |
| 2 | $Cr(NO_3)_3$ | $Cr_xAl_{1-x}q_3$ | $Cr_{0.05}Al_{0.95}q_3$ | 5% |
| 3 | $Y(NO_3)_3$ | $Y_xAl_{1-x}q_3$ | $Y_3Al_5q_3$ | 38% |
| 4 | $Sr(NO_3)_2$ | $Sr_xAl_{1-x}q_3$ | $Sr_{0.33}Al_{0.66}q_3$ | 33% |
| 5 | $Co(NO_3)_3$ | $Co_xAl_{1-x}q_3$ | $Co_{0.3}Al_{0.7}q_3$ | 30% |

The solid solutions were analyzed by powder x-ray diffraction (XRD) and scanning electron microscopy (SEM). The XRD patterns of all the solid solutions were very similar, strongly resembling the XRD pattern of Alq$_3$, thus indicating that each solid solution was isomorphous in nature and further that each possessed the crystallographic morphology of Alq$_3$. Thus, the solid solutions are isostructural with that of Alq$_3$.

SEM microscopy analysis of the solid solutions revealed the solid solutions to be highly crystalline materials, like Alq$_3$. While the shape and morphology varied with the composition, the crystals of any given solid solution were generally unagglomerated and monodisperse in size. La$_{0.5}$Al$_{0.5}$q$_3$ crystals were nearly spherical in shape with diameters of approximately 20-100 nm The crystals of Y$_3$Al$_5$q$_3$ were ellipsoid, with minor axis distances of approximately 200-500 nm and major axis distances of approximately 500-1500 nm.

The solubilities of the solid solutions were evaluated (Table 2). In general, each solid solution exhibited at least some solubility in ethanol, dichloromethane, N,N-dimethylformamide (DMF), or chloroform. Solubility of the solid solutions is a useful property for production of thin films and fibers of the precursors, and thus thin films and fibers of doped aluminum oxides.

TABLE 2

Solubilities of Alq$_3$ and the Solid Solutions.

| Entry | Alq$_3$ or Solid Solution | Solubility* | | | |
|---|---|---|---|---|---|
| | | C$_2$H$_5$OH | CH$_2$Cl$_2$ | DMF | CHCl$_3$ |
| 1 | Alq$_3$ | NS | PS | PS | PS |
| 2 | Cr$_{0.05}$Al$_{0.95}$q$_3$ | PS | PS | VS | PS |
| 3 | Co$_{0.3}$Al$_{0.7}$q$_3$ | NS | PS | NS | NS |
| 4 | Y$_3$Al$_5$q$_3$ | PS | PS | PS | PS |
| 5 | La$_{0.5}$Al$_{0.5}$q$_3$ | PS | VS | VS | PS |
| 6 | Sr$_{0.33}$Al$_{0.66}$q$_3$ | PS | VS | VS | VS |

*NS: not soluble; PS: partially soluble; VS: very soluble

Example 2

General preparation of aluminum oxide and doped aluminum oxides. In general, Alq$_3$ (Example 1A) or the solid solutions (Example 1B) may be decomposed with heating and/or calcination in the presence of air or oxygen to give Al$_2$O$_3$ or the corresponding doped aluminum oxides respectively. Typically, the heating or calcination was performed below 600° C., usually between 400-600° C. Depending on the manner of processing the solid solutions (or Alq$_3$), doped aluminum oxides (or Al$_2$O$_3$) may be obtained in various forms, including powders, films, or fibers. Notably, regardless of the form, the composition of the doped aluminum oxides remains the same. The procedures for obtaining these various forms of doped aluminum oxides from their solid solution counterparts are detailed below.

Example 2A

Preparation of bulk powders from solid solutions. Direct calcination of Alq$_3$ (Example 1A) or the solid solutions (Example 1B) afforded the corresponding Al$_2$O$_3$ or doped aluminum oxides in the form of bulk powders as indicated in Table 3.

TABLE 3

Bulk Powders Prepared Through Calcination of Alq$_3$ or Solid Solutions

| Entry | Alq$_3$ or Solid Solution | Bulk Powder | Application |
|---|---|---|---|
| 1 | Alq$_3$ | Al$_2$O$_3$ | Laser host material |
| 2 | La$_{0.5}$Al$_{0.5}$q$_3$ | LaAlO$_3$ ("perovskite") | Single crystal substrate/Phosphor |
| 3 | Cr$_{0.05}$Al$_{0.95}$q$_3$ | Cr:Al$_2$O$_3$ ("ruby") | Lasing material |
| 4 | Y$_3$Al$_5$q$_3$ | Y$_3$Al$_5$O$_{12}$ ("YAG") | Lasing material |
| 5 | Sr$_{0.33}$Al$_{0.66}$q$_3$ | SrAl$_2$O$_4$ | Phosphors |
| 6 | Co$_{0.3}$Al$_{0.7}$q$_3$ | CoAl$_2$O$_4$ | Pigment |

The doped aluminum oxides were analyzed by x-ray diffraction (XRD) and scanning electron microscopy (SEM). The XRD diffractograms revealed the various doped aluminum oxides to be single phase, highly crystalline and chemically homogeneous. The XRD patterns of all the doped aluminum oxide powders were very similar, closely resembling the XRD pattern of undoped Al$_2$O$_3$, thus indicating that each doped aluminum oxide was isomorphous in nature and further that each possessed the crystallographic morphology of Al$_2$O$_3$. Thus, the doped aluminum oxides were isostructural with that of undoped Al$_2$O$_3$.

SEM microscopy confirmed the doped aluminum oxides to be highly crystalline, and further indicated the morphology, size, and shape of the crystallites to be strongly dependent on the identity of the solid solution. Most of the crystallites were approximately 100 nm or larger.

A photoluminescence spectrum was recorded for chromium-doped aluminum oxide powder, Cr:Al$_2$O$_3$ (entry 3, Table 3). As shown in FIG. 1, a sharp emission peak was observed at 692.2 nm, and was attributed to a $^2E \rightarrow {}^4A_2$ spin-forbidden electronic transition. Notably, this red emission wavelength is identical to that of the literature values for absorption ($^4A_2 \rightarrow {}^2E$) and fluorescence ($^2E \rightarrow {}^4A_2$) of ruby. The 692.2 nm emission is fundamental to the lasing action of a ruby laser. Thus, this data indicates the ability of the present technology to atomically dope aluminum oxide in a controlled and homogeneous fashion to give ruby powder.

Example 2B

Preparation of thin films generally. Thin films of either the solid solutions or the doped aluminum oxides are easily prepared. In such a process, a solid solution is dissolved in a suitable solvent (including, but not limited to, those indicated in Table 2) and cast into a thin film on to a substrate using conventional casting methods, including spin-casting. Where necessary to increase solubility of the solid solution, mixed solvent systems may be employed. Calcination of the solid solution thin film provides the corresponding doped aluminum oxide in film form. The doped aluminum oxide thin film formed in this manner will have the same composition as that of the corresponding bulk powder.

Example 2C

Preparation of fibers generally. Fibers (including nanofibers and wires) of the solid solutions and doped aluminum oxides may be readily obtained through conventional electrospinning techniques. In this procedure, a solid solution is combined with a polymer such as polyvinylpyrrolidone or polyvinyl alcohol to form a polymer composite. The resultant polymer composite is then electrospun to yield polymer composite fibers. The polymer composite fibers are further calcined to produce doped aluminum oxide fibers.

Preparation of Alq$_3$ and Al$_2$O$_3$ nanofibers through spin-casting of Alq$_3$-polymer composites. Alq$_3$ (1.0 g) was dissolved in a minimum quantity of dichloromethane (4 mL) to provide a first solution. To this first solution was added a second solution of a polymer (either polyvinylpyrrolidone (8.0 g) or polyvinyl alcohol (7.5 g)) in dichloromethane (20 mL). The resultant solution was stirred at room temperature for 1-2 hours, then loaded into a plastic syringe and further injected into an electrospinning apparatus at an applied voltage of 12-15 kV to provide Alq$_3$-polymer composite nanofibers of either Alq$_3$-polyvinylpyrrolidone or Alq$_3$-polyvinyl alcohol depending on the polymer used. The resultant nanofibers were collected on aluminum foil or silicon wafers. The nanofibers were calcined at a temperature of 400° C. for a period of about 2 hours to remove the polymer matrix and any other volatile materials. The nanofibers were further calcined at temperature of 600° C. for a period of about 5 hours to provide Al$_2$O$_3$ nanofibers. The above procedure may be extended to polymer composites including the solid solutions to provide nanofibers of the solid solution-polymer composite, as well as nanofibers of doped aluminum oxides.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

Other embodiments are set forth in the following claims.

The invention claimed is:

1. A process of preparing a doped aluminate, the process comprising:
providing a solution comprising 8-hydroxyquinoline; an aluminum precursor; a dopant precursor, and a reaction solvent;
isolating a precipitate from the solution; and
calcining the precipitate to form the doped aluminate.

2. The process of claim 1, wherein the dopant precursor is a metal salt or metal alkoxide.

3. The process of claim 1, wherein the dopant precursor is a metal salt or metal alkoxide of chromium, manganese, iron cobalt, nickel, lanthanum, cerium, praseodymium, neodymium, promethium, samarium, europium, gadolinium, terbium, dysprosium, holmium, erbium, thulium, ytterbium, lutetium, yttrium, calcium, magnesium, barium, or strontium.

4. The process of claim 1, wherein the aluminum precursor is an aluminum salt, an aluminum alkoxide, or a mixture of any two or more thereof.

5. The process of claim 1, wherein the aluminum precursor is aluminum chloride, aluminum bromide, aluminum methoxide, aluminum ethoxide, aluminum acetate, aluminum isopropoxide, aluminum nitrate, or a mixture of any two or more thereof.

6. The process of claim 1, wherein the aluminum precursor is a compound of formula Al(OR)$_3$, where R is a C$_1$-C$_{10}$ alkyl, or an aryl group.

7. The process of claim 6, wherein R is methyl, ethyl, n-propyl, or isopropyl.

8. The process of claim 1, wherein the reaction solvent is an alcohol, an ether, a glycol ether, a ketone, an amide, a nitrile, a halogenated hydrocarbon, or a mixture of any two or more thereof.

9. The process of claim 1, further comprising heating the solution at a temperature, and for a time period, sufficient to produce the precipitate, prior to the isolating step.

10. The process of claim 9, wherein the temperature is the refluxing temperature of the reaction solvent.

11. The process of claim 9, wherein the time period is about 10 minutes to about 10 hours.

12. The process of claim 1, further comprising washing the precipitate with a wash solvent before the calcining step and after the isolating step.

13. The process of claim 12, wherein the wash solvent is an alcohol or an ether.

14. The process of claim 1, wherein the doped aluminate is LaAlO$_3$ (perovskite), Y$_3$Al$_5$O$_{12}$ (yttrium aluminum garnet), Cr:Al$_2$O$_3$, CoAl$_2$O$_4$, or SrAl$_2$O$_4$.

15. The process of claim 1 further comprising combining the precipitate with a polymer after the isolating step and before the calcining step to form a polymer composite.

16. The process of claim 15, wherein the polymer is polyvinylpyrrolidone or polyvinyl alcohol.

17. The process of claim 15 further comprising preparing a nanofiber of the polymer composite before the calcining step.

18. The process of claim 15, further comprising preparing a nanofiber of the polymer composite before the calcining step by electrospinning the polymer composite into nanofibers.

* * * * *

UNITED STATES PATENT AND TRADEMARK OFFICE
CERTIFICATE OF CORRECTION

| | | |
|---|---|---|
| PATENT NO. | : 8,524,178 B2 | Page 1 of 1 |
| APPLICATION NO. | : 13/321146 | |
| DATED | : September 3, 2013 | |
| INVENTOR(S) | : Manoharan | |

It is certified that error appears in the above-identified patent and that said Letters Patent is hereby corrected as shown below:

On the Title Page, in Item (56), under "OTHER PUBLICATIONS", in Column 1, at Line 14, insert -- International Search Report and Written opinion for PCT/IB2011/051642 mailed August 2, 2011. --.

On the Title Page, in Item (56), under "OTHER PUBLICATIONS", in Column 1, Line 36, delete "tris(8-hdroxyquinoline)" and insert -- tris(8-hydroxyquinoline) --, therefor.

In the Specification

In Column 3, Line 41, delete "thereof" and insert -- thereof. --, therefor.

In Column 3, Line 48, delete "thereof" and insert -- thereof. --, therefor.

In Column 4, Line 18, delete "8-hydroxyquinolato" and insert -- 8-hydroxyquinolinato --, therefor.

In Column 6, Line 23, delete "Alga" and insert -- Alq$_3$ --, therefor.

In Column 7, Line 12, delete "nm" and insert -- nm. --, therefor.

In the Claims

In Column 10, Lines 34-35, in Claim 3, delete "iron cobalt" and insert -- iron, cobalt --, therefor.

Signed and Sealed this
Eighth Day of April, 2014

Michelle K. Lee
*Deputy Director of the United States Patent and Trademark Office*